US008758424B2

(12) United States Patent
Sachar et al.

(10) Patent No.: US 8,758,424 B2
(45) Date of Patent: *Jun. 24, 2014

(54) PERCUTANEOUS TRANSLUMINAL ANGIOPLASTY DEVICE WITH INTEGRAL EMBOLIC FILTER

(71) Applicant: Contego Medical, LLC, Raleigh, NC (US)

(72) Inventors: Ravish Sachar, Raleigh, NC (US); Greg Sutton, Maple Grove, MN (US); Larry A. Roberts, Atlanta, GA (US)

(73) Assignee: Contego Medical, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/850,782

(22) Filed: Mar. 26, 2013

(65) Prior Publication Data

US 2013/0226225 A1 Aug. 29, 2013

Related U.S. Application Data

(63) Continuation of application No. 10/997,803, filed on Nov. 24, 2004, now Pat. No. 8,403,976.

(60) Provisional application No. 60/560,934, filed on Apr. 8, 2004.

(51) Int. Cl.
*A61F 2/06* (2013.01)

(52) U.S. Cl.
USPC ........................................ 623/1.11; 606/200

(58) Field of Classification Search
USPC ......... 606/113, 114, 127, 200; 623/1.11, 1.12
See application file for complete search history.

(56) References Cited

U.S. PATENT DOCUMENTS

| 4,723,549 | A | * | 2/1988 | Wholey et al. ................. 606/194 |
| 5,456,667 | A | * | 10/1995 | Ham et al. ..................... 604/107 |
| 5,653,684 | A | * | 8/1997 | Laptewicz et al. ............. 604/22 |
| 6,511,503 | B1 | * | 1/2003 | Burkett et al. ................ 623/1.11 |
| 6,761,732 | B2 | * | 7/2004 | Burkett et al. ................ 623/1.11 |
| 7,722,634 | B2 | * | 5/2010 | Panetta et al. ................. 606/200 |
| 8,052,731 | B2 | * | 11/2011 | Soltis et al. ................... 623/1.11 |
| 2003/0055480 | A1 | * | 3/2003 | Fischell et al. ............... 623/1.11 |
| 2003/0093106 | A1 | * | 5/2003 | Brady et al. .................. 606/194 |
| 2003/0176884 | A1 | * | 9/2003 | Berrada et al. ................ 606/200 |
| 2004/0236368 | A1 | * | 11/2004 | McGuckin et al. ........... 606/200 |
| 2005/0038468 | A1 | * | 2/2005 | Panetta et al. ................ 606/200 |

* cited by examiner

*Primary Examiner* — Ryan Severson
*Assistant Examiner* — David Eastwood
(74) *Attorney, Agent, or Firm* — Ballard Spahr LLP

(57) ABSTRACT

A percutaneous transluminal angioplasty device having an embolic filter mounted to the catheter shaft at a location distal to the angioplasty balloon and downstream from the blockage to capture embolic particles that may be set loose into the blood stream as the angioplasty procedure is performed. The embolic filter is normally collapsed against the catheter shaft to facilitate introduction and withdrawal of the device to and from the operative site. Once the angioplasty balloon is properly positioned, however, means operatively associated with the embolic filter are actuated to erect the filter to operatively position a filter mesh across the lumen of the vessel.

24 Claims, 19 Drawing Sheets

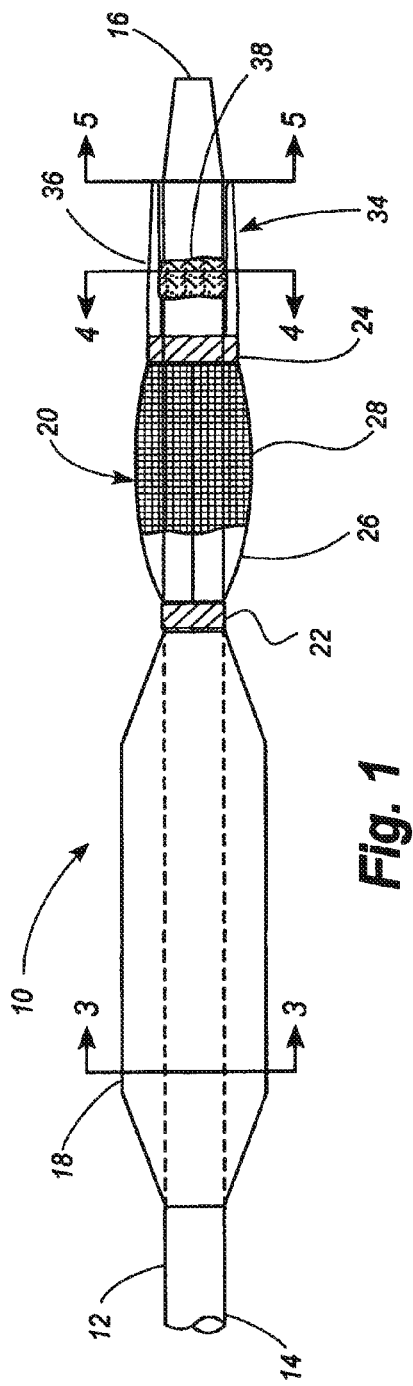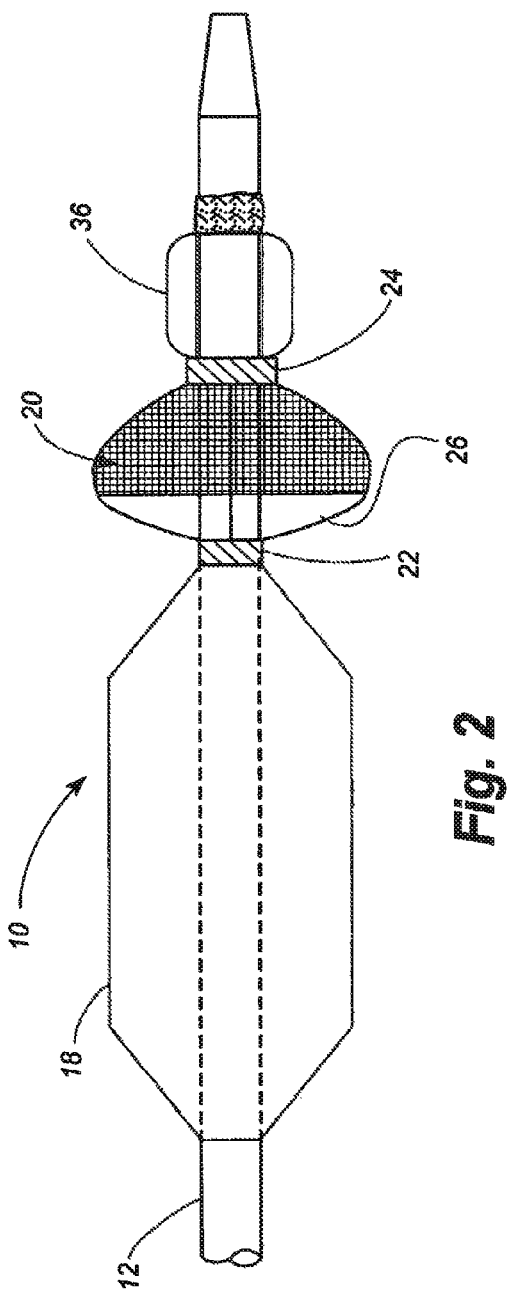

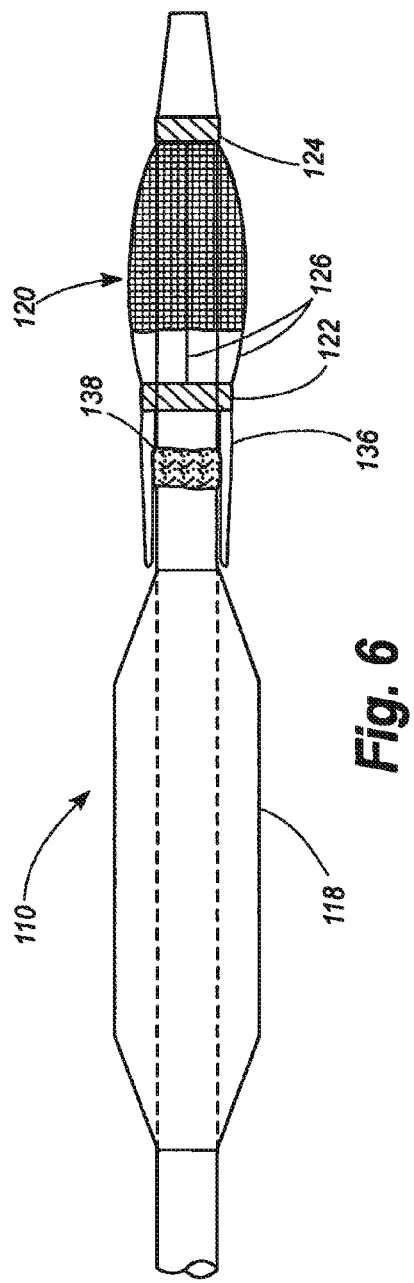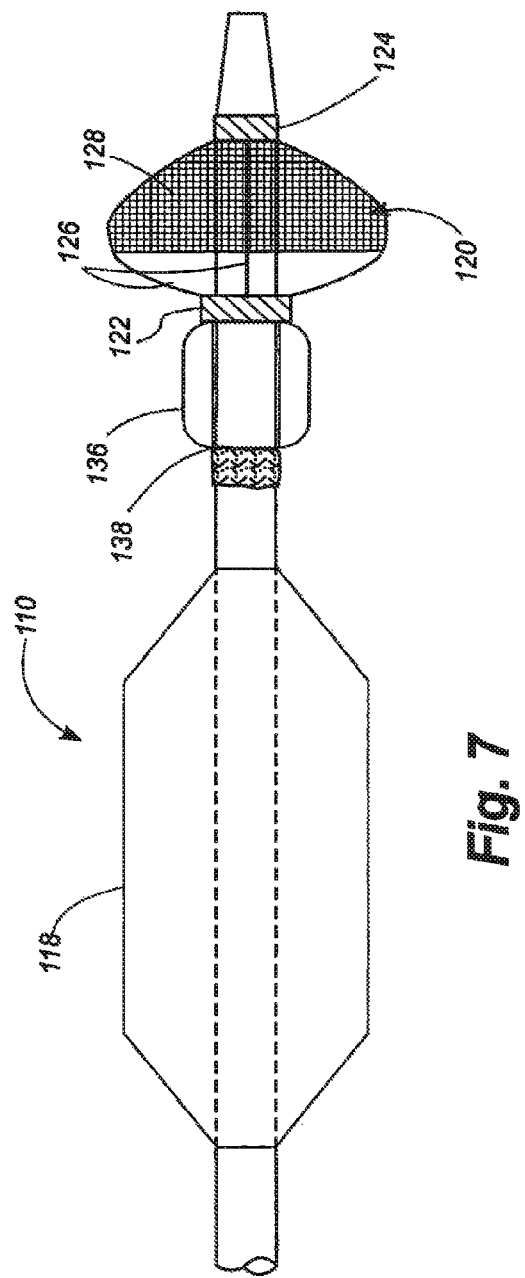

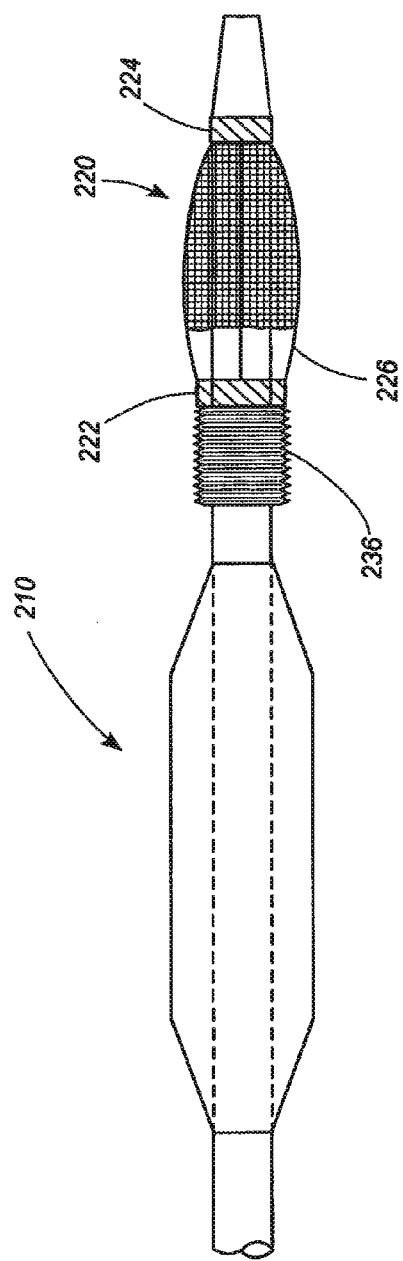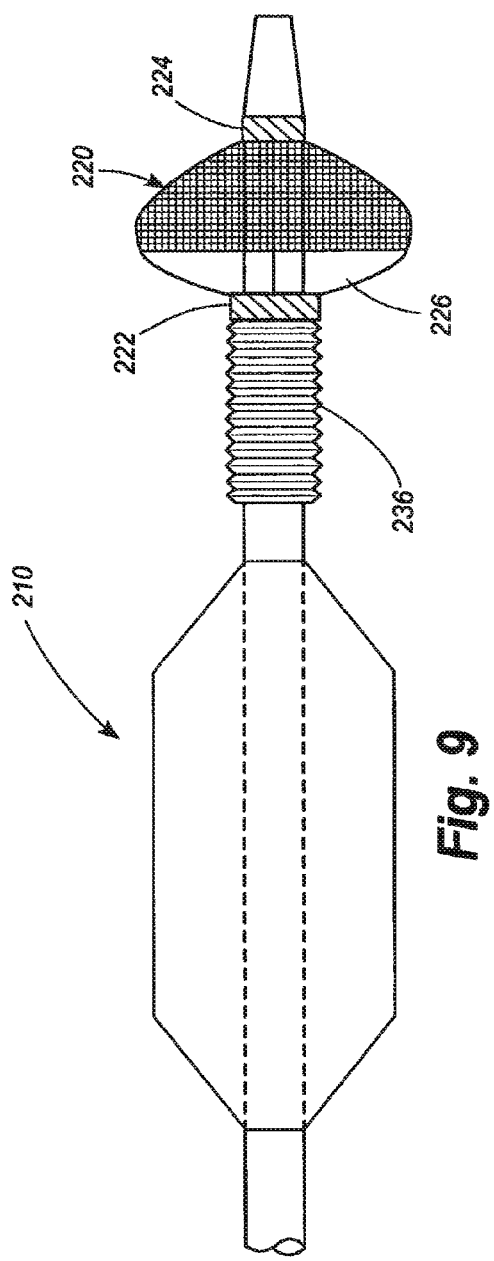

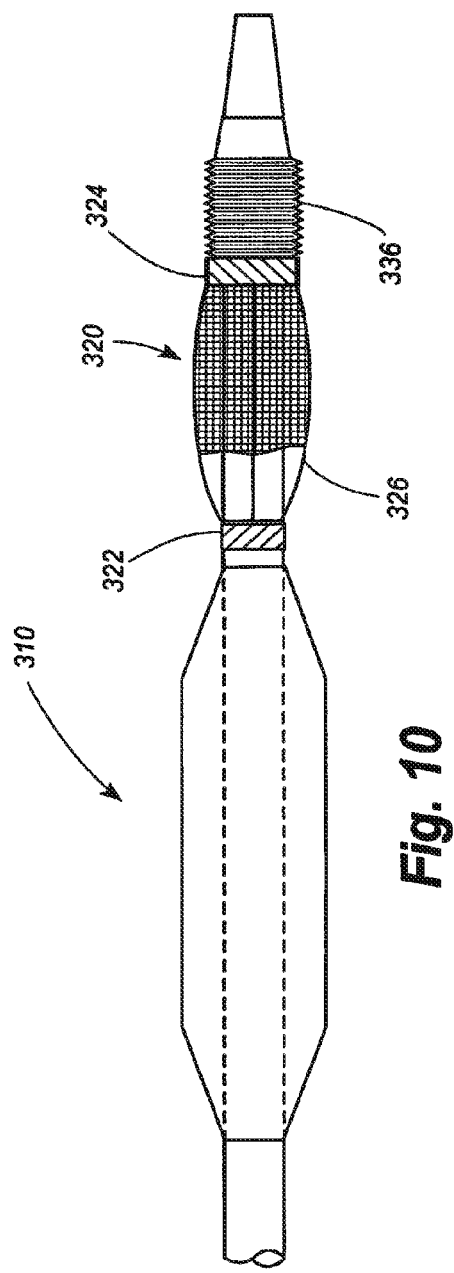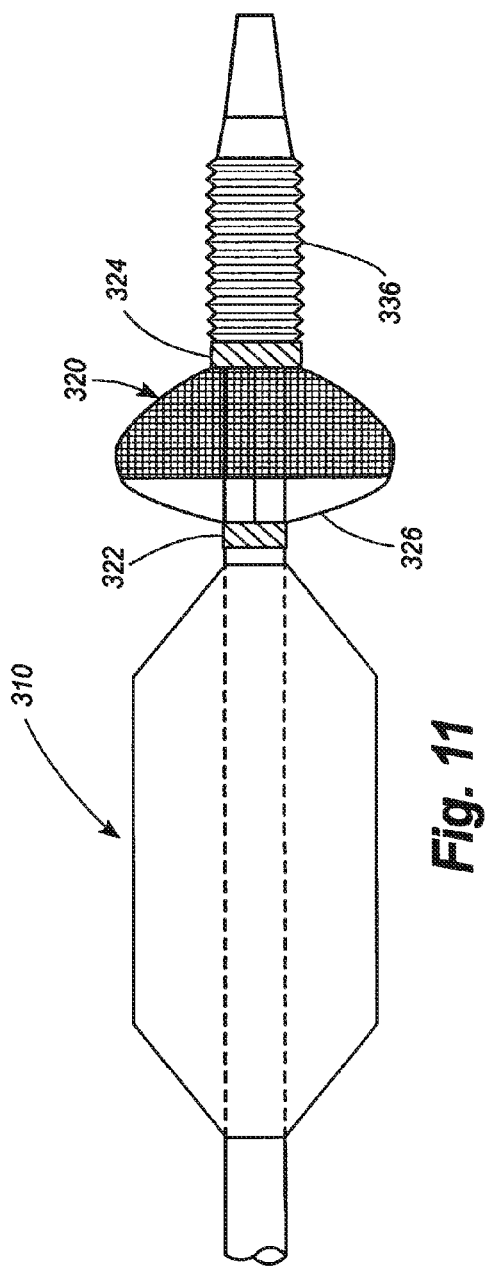

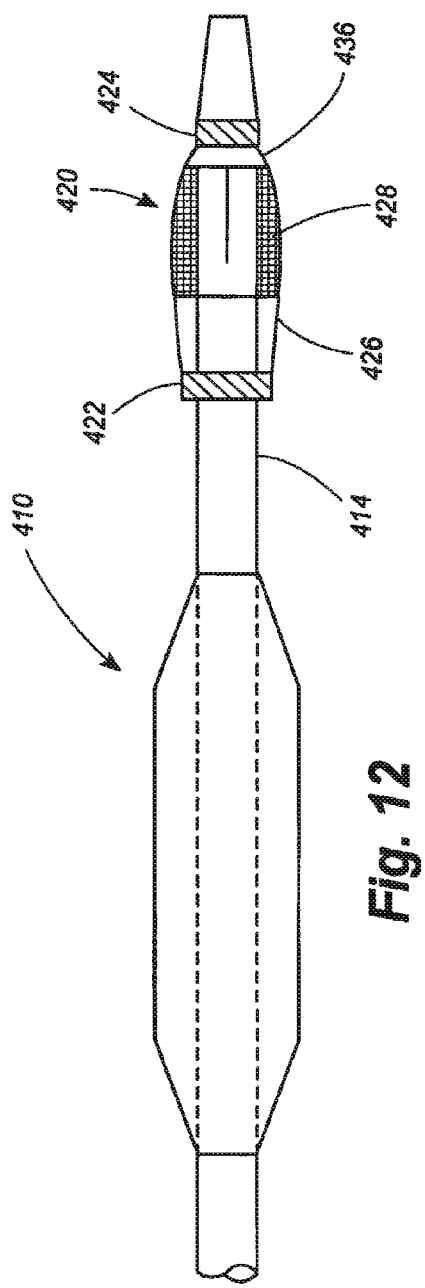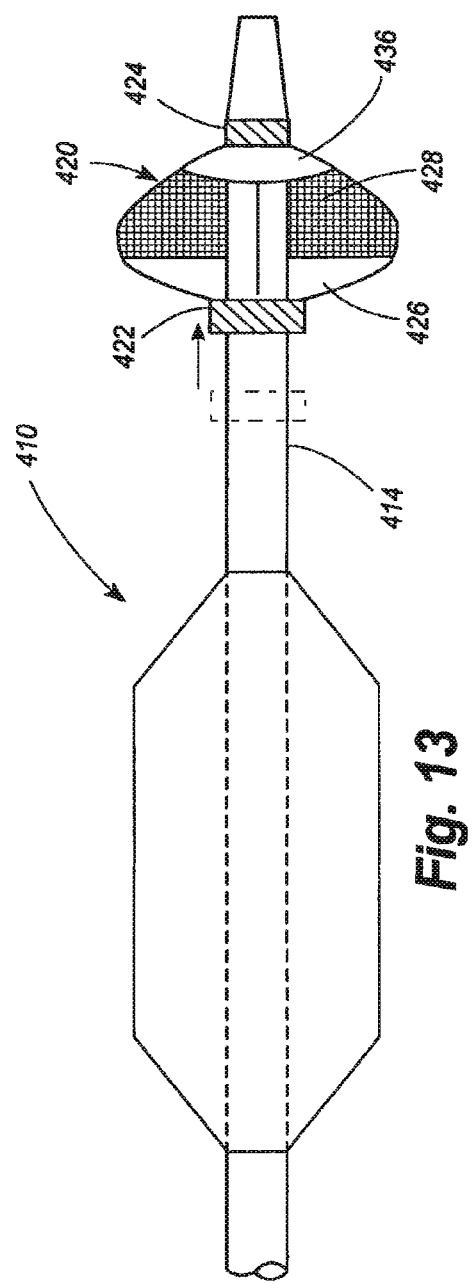

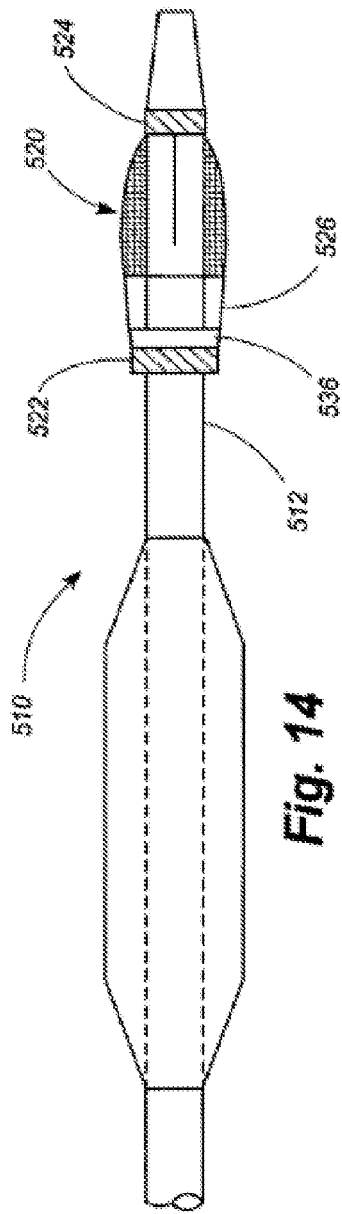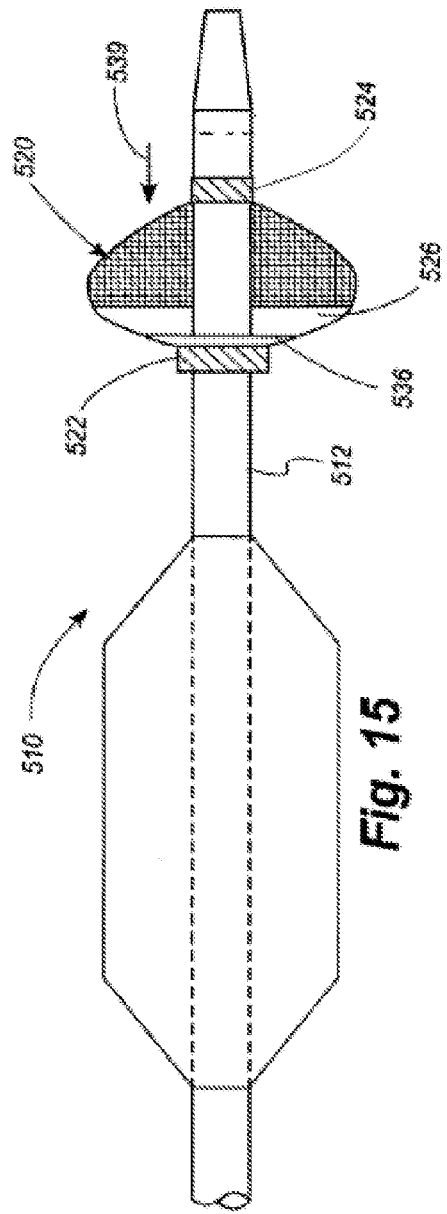

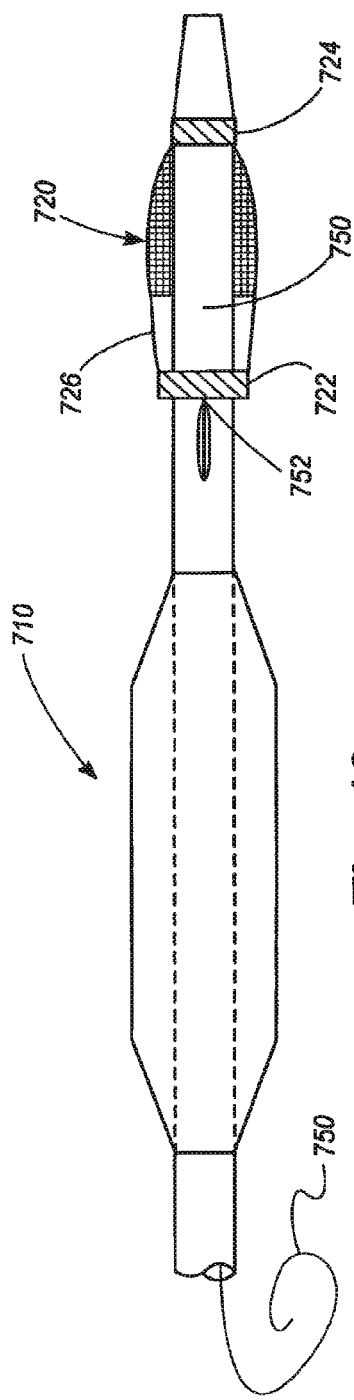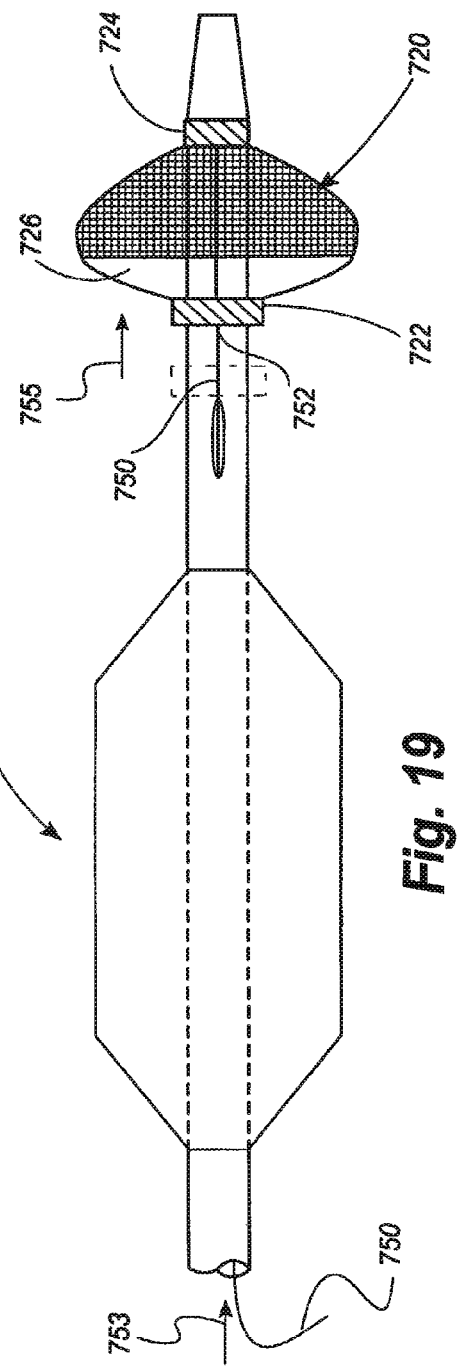

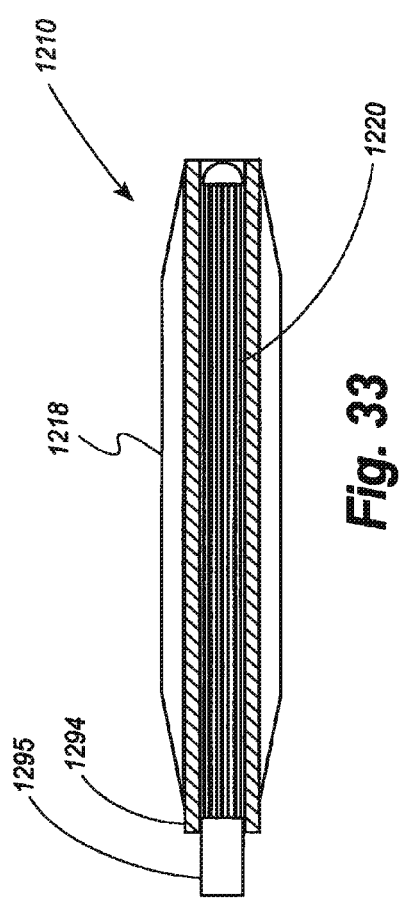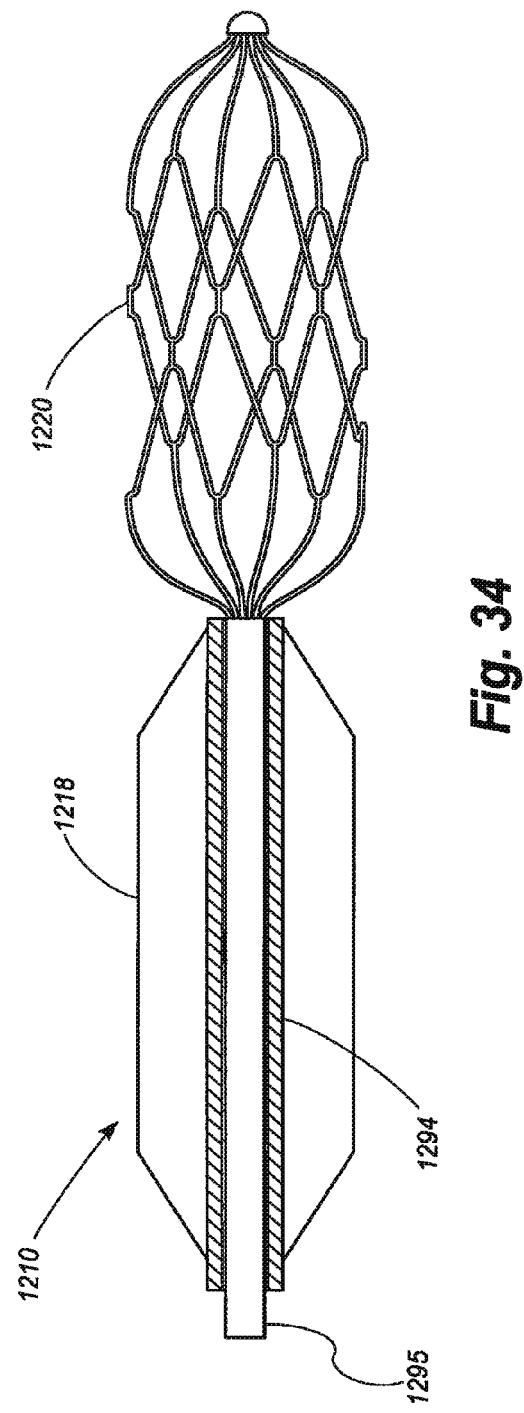

PERCUTANEOUS TRANSLUMINAL ANGIOPLASTY DEVICE WITH INTEGRAL EMBOLIC FILTER

CROSS-REFERENCE TO RELATED APPLICATION

This application is a Continuation of U.S. application Ser. No. 10/997,803, filed Nov. 24, 2004, now U.S. Pat. No. 8,403,976 issued Mar. 26, 2013, which claims benefit of U.S. Provisional Application No. 60/560,934, filed Apr. 8, 2004, which applications are herein incorporated by reference in their entirety.

FIELD OF THE INVENTION

The present invention relates generally to surgical devices and relates more specifically to a percutaneous transluminal angioplasty device.

BACKGROUND OF THE INVENTION

The vascular bed supplies a constant flow of oxygen-rich blood to the organs. If plaque builds up in these vessels, blockages can develop, reducing blood flow to the organs and causing adverse clinical symptoms, up to and including fatality.

Angioplasty is a catheter-based procedure performed by a physician to open up a blocked vessel and restore blood flow. An entry site is opened, for example in the patient's groin, arm, or hand, and a guide wire and catheter are advanced under fluoroscopic guidance to the location of the blockage. A catheter having a small balloon adjacent its distal end is advanced under fluoroscopic guidance until the balloon lies within the stenosed region. The balloon is then inflated and deflated one or more times to expand the stenosed region of the artery.

Since diseased vessels are comprised of a range of material from early-stage thrombosis to late-stage calcified plaque, angioplasty can release embolic particles downstream from the stenosed location. These embolic particles can result in adverse clinical consequences. It has been shown that it is beneficial to trap these embolic particles to prevent them from traveling downstream with blood flow to the capillary bed (e.g., Bairn D S, Wahr D, George B, et al., *Randomized Trial of a Distal Embolic Protection Device During Percutaneous Intervention of Saphenous Vein Aorto-Coronary Bypass Grafts*, Circulation 2002; 105:1285-90).

In addition to balloon angioplasty, stenoses may also be treated with stents and with mechanical thrombectomy devices. These devices are also prone to releasing embolic particles downstream from the stenosed location.

There are systems available today that are used to catch these embolic particles. They are primarily filter systems or occlusion balloon systems built on a guidewire. These systems have shortcomings related to simplicity of use and crossing tight lesions with a filter or balloon guidewire that is larger in diameter than the guide wire which is normally used. These embolic protection guidewires also have flexibility and stability problems that make the protected angioplasty procedure difficult in many cases. In the case of saphenous vein grafts, the problems relate specifically to aorto-ostial lesions, where the guidewire may not be long enough to provide support, or distal vein graft lesions, where there is not enough of a landing zone for the filter. The latter is a problem as currently available filter systems have a considerable distance between the treatment balloon and the distal filter. This distance is a problem not only in distal vein graft lesions, but also in arterial stenoses in which there is a side branch immediately after the stenosis. In such cases, the filter can often be deployed only distal to the side branch, thus leaving the side branch unprotected from embolic particles.

SUMMARY

Stated generally, the present invention comprises a percutaneous transluminal angioplasty device with integral embolic filter. Because the filter is integral with the catheter of the angioplasty device, there is no need to insert a separate device into the vessel. Further, proper placement of the angioplasty balloon assures proper placement of the embolic filter.

Stated somewhat more specifically, the percutaneous transluminal angioplasty device of the present invention comprises an embolic filter mounted to the catheter shaft at a location distal to the angioplasty balloon, stent, or mechanical thrombectomy device. Thus the filter is downstream from the blockage and is properly positioned to capture embolic particles that may be set loose into the blood stream as the angioplasty procedure is performed. The embolic filter is normally collapsed against the catheter shaft to facilitate introduction and withdrawal of the device to and from the operative site. Once the angioplasty balloon, stent, or mechanical thrombectomy device is properly positioned, however, means operatively associated with the embolic filter are actuated to erect the filter to position a filter mesh across the lumen of the coronary artery.

In some embodiments the means for erecting the filter comprises a balloon which longitudinally displaces one end of the filter toward the other, causing longitudinal ribs to bow outward, thus erecting the filter mesh. In other embodiments the means for erecting the filter comprises a balloon interposed within the proximal and distal ends of the filter, whereby inflating the balloon will bias the ribs away from the catheter shaft, causing the ribs to bow outwardly to erect the filter mesh. In still other embodiments the means for erecting the filter comprises a pull wire attached to one end of the filter, such that pulling on the wire longitudinally displaces one end of the filter toward the other, causing longitudinal ribs to bow outward, thus erecting the filter mesh.

In one embodiment of the invention, a reservoir is provided at the distal tip of the filter so that when the device collapses for withdrawal, debris does not get pushed out of the filter.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention.

FIG. 1 is a partial cut away side view of first embodiment of a percutaneous transluminal angioplasty device according to a first embodiment of the disclosed invention, with the angioplasty balloon and embolism filter in their collapsed positions.

FIG. 2 is a partial cut away side view of the percutaneous transluminal angioplasty device of FIG. 1 showing the angioplasty balloon and embolism filter in their erected positions.

FIG. 6 is a second embodiment of a percutaneous transluminal angioplasty device according to the present invention, which differs from the percutaneous transluminal angioplasty of FIGS. 1 and 2 in that the actuation balloon is on the proximal side of the embolic filter, and the filter erects from a different direction.

FIG. 7 is a view of the percutaneous transluminal angioplasty device of FIG. 6 showing the angioplasty balloon inflated and the embolic filter erected.

FIG. 8 is a third embodiment of a percutaneous transluminal angioplasty device and differs from the previously described embodiments in that the means for erecting the embolic filter is a bellows. FIG. 8 shows the angioplasty balloon and the embolic filter in their collapsed positions.

FIG. 9 IS another view of the percutaneous transluminal angioplasty device of FIG. 8 showing the angioplasty balloon and the embolic filter in their inflated or raised positions.

FIG. 10 is another embodiment of a percutaneous transluminal angioplasty device according to the present invention which employs a bellows to raise and lower the embolic filter. The embodiment of FIG. 10 differs from the embodiment of FIGS. 8 and 9 in that the bellows is disposed on the distal end of the filter such that the filter opens from the opposite direction. FIG. 10 shows the angioplasty balloon and the embolic filter in their deflated or collapsed positions.

FIG. 11 is another view of the percutaneous transluminal angioplasty device of FIG. 10, showing the angioplasty balloon inflated and the embolic filter raised.

FIG. 12 shows still another embodiment of a percutaneous transluminal angioplasty device according to the present invention, in which the balloon interposed between the catheter shaft and the ribs forces the ribs upward, thereby causing them to bow into the erected embolic filter. FIG. 12 shows the device with the angioplasty balloon and the embolic filter in their collapsed or lowered positions.

FIG. 13 is another view of the percutaneous transluminal angioplasty device of FIG. 12, showing the angioplasty balloon in its inflated condition and the embolic filter in its erected condition.

FIG. 14 is another embodiment of a percutaneous transluminal angioplasty device according to the present invention. This embodiment differs from the embodiments of FIGS. 12 and 13 in that the balloon is located at the opposite end of the filter. Nonetheless, when inflated, the balloon forces the ribs away from the shaft and into their accurate positions, thereby raising the embolic filter. FIG. 14 shows the embodiment with the angioplasty balloon collapsed and the embolic filter retracted against the catheter shaft.

FIG. 15 is another view of the embodiment of FIG. 14, showing the angioplasty balloon inflated and the embolic filter erected.

FIG. 16 shows the device with the angioplasty balloon deflated and the embolic filter collapsed against the catheter shaft.

FIG. 18 is another embodiment of a percutaneous transluminal angioplasty device according to the present invention, showing the angioplasty balloon and the embolic filter in their collapsed conditions.

FIG. 19 is another view of the embodiment of FIG. 18, showing the angioplasty balloon inflated and the embolic filter raised.

FIG. 33 is a side cutaway view of another embodiment of an angioplasty device showing an angioplasty balloon in its deflated condition and an embolic filter in a retracted state.

FIG. 34 is a side cutaway view of the angioplasty device of FIG. 33 showing the angioplasty balloon inflated and the embolic filter erected.

DETAILED DESCRIPTION OF THE DISCLOSED EMBODIMENTS

Figure 3:
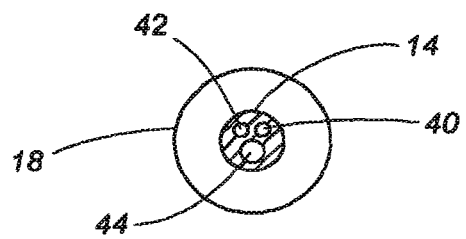
FIG. 3 is a cross sectional view taken along line 3-3 of FIG. 1.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "lumen" can include two or more such lumens unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The present invention can be understood more readily by reference to the following detailed description of preferred embodiments of the invention and the examples included therein and to the Figures and their previous and following description.

Referring now to the drawings, FIGS. 1 and 2 illustrate a first embodiment of a percutaneous transluminal angioplasty device 10 according to the present invention. The device 10 comprises an elongated catheter 12 having a shaft 14 with a proximal end (not shown) and a distal end 16. Spaced a short distance proximally from the distal end 16 of the catheter 12 is an angioplasty balloon 18 of conventional design. In FIG. 1 the angioplasty balloon 18 is shown in a deflated or collapsed condition. In FIG. 2 the angioplasty balloon 18 is shown in an inflated condition.

Located between the angioplasty balloon 18 and the distal tip 14 of the catheter 12 is a collapsible filter 20. The filter 20 includes a proximal ring portion 22 and a distal ring portion 24. A plurality of elongated ribs 26 extend generally longitudinally between the proximal and distal rings 22, 24. These ribs can be made of a shape memory material, such as nitinol, and in their baseline position, these ribs are collapsed. A filter mesh 28 overlies the distal portion of the ribs 26. In the embodiment of FIGS. 1 and 2, the distal ring 24 is movable toward and away from the proximal ring 22. As the distal ring 24 moves toward the proximal ring 22, the ribs 26 bow outward. As the ribs 26 bow outward, the filter mesh 28 overlaying the ribs is erected. FIG. 1 shows the filter 20 in its collapsed condition, while FIG. 2 shows the filter in its erected condition.

Means 34 are included for erecting and collapsing the filter 20 of the device 10 shown in FIGS. 1 and 2. Specifically a balloon 36 has its distal end 38 bonded to the shaft 14 of the catheter 12. When the distal ring 24 is in its withdrawn position, as shown in FIG. 1, the bulk of the balloon 36 is folded forward over the shaft 14 of the catheter 12. When the balloon 36 is inflated, as shown in FIG. 2, the balloon 36 expands proximally, pushing the distal ring 24 in a proximal direction, causing the ribs 26 to bow outward and thereby erecting the filter 20. When the balloon 32 is deflated, the shape memory ribs straighten, urging the distal ring 24 in a distal direction and collapsing the filter 20 close to the shaft 14 of the catheter 12.

Figure 4:
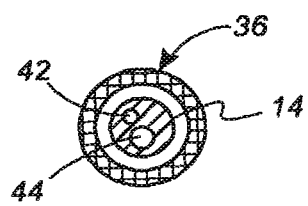
FIG. 4 is a cross sectional view taken along line 4-4 of FIG. 1.
Figure 5:
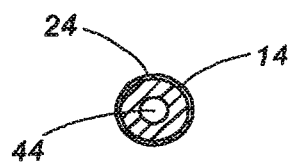
FIG. 5 is a cross sectional view taken along line 5-5 of FIG. 1.

FIGS. 3, 4, and 5 show cross sections of the device 10 at various locations along its length. Referring first to FIG. 3, the catheter shaft 12 has three lumens: two smaller lumens and a large main lumen. The two smaller lumens are inflation lumens, one lumen 40 for the angioplasty balloon 18, and one lumen 42 for the balloon 36 which controls the filter 20. The larger main lumen 44 is used to receive a guide wire (not shown) over which the device 10 advanced to position the device for performing an angioplasty procedure.

Referring now to FIG. 4, this cross section is taken at a location distal to the angioplasty balloon 18. Consequently, the angioplasty balloon inflation lumen 40 has terminated and is no longer visible. Thus, FIG. 4 shows only two lumens, the main lumen 44 for receiving the guide wire, and the smaller inflation lumen 42 for the filter balloon 36.

Referring now to FIG. 5, this cross section is taken at a location distal to the filter balloon 36, and hence only the main lumen 44 is visible.

FIGS. 6 and 7 show an alternate embodiment of a percutaneous transluminal angioplasty device 110 according to the present invention. This device is similar to the device 10 previously described, with the exception that the filter 120, in this case, has its distal ring 124 fixed, and the proximal ring 122 of the filter 120 is movable toward and away from the distal ring to cause the ribs 126 to bow outwardly or to straighten. The balloon 136 is located on the proximal side of the filter 120 and pushes the proximal ring 122 in a distal direction when the balloon 136 is inflated.

Referring now to FIGS. 8 and 9, yet another alternate embodiment of percutaneous transluminal angioplasty device 210 is shown. This device is similar to the device shown in FIGS. 1 and 2, with the exception that the means for erecting the filter 220 is a bellows 236, instead of a balloon. In FIG. 8, the bellows 236 is un-inflated and hence it is in a collapsed condition, permitting the ribs 226 of the filter 220 to straighten out against the shaft 214 of the catheter 212. In FIG. 9, the bellows 236 has been inflated, pushing the proximal ring 222 in a distal direction, bowing out the ribs 236 and erecting the filter mesh 238.

FIGS. 10 and 11 illustrate still another embodiment of a percutaneous transluminal angioplasty device 310. This device is similar to the device shown in FIGS. 8 and 9, with the exception that the bellows 336 is placed on the distal side of the filter 320. Thus, when the bellows 336 is inflated, it moves the distal ring 324 in a proximal direction toward the proximal ring 322, thereby causing the ribs 326 to bow outwardly, erecting the filter mesh 338.

FIGS. 12 and 13 depict another embodiment of a percutaneous transluminal angioplasty device 410. In this device the means for erecting the filter comprises a balloon 436 disposed between the catheter shaft 414 and the ribs 426 adjacent the fixed distal ring 424 of the filter 420. When the balloon 436 is inflated, it forces the ribs 426 outward away from the catheter shaft 414, thereby bowing the ribs and drawing the proximal ring 422 of the filter 420 in a distal direction. As the ribs 426 bow outward, the filter mesh 428 is erected, thereby raising the filter 420.

FIGS. 14 and 15 show a device 510 similar to that shown in FIGS. 12 and 13, with the exception that the balloon 536 is placed between the catheter shaft 512 and the ribs 526 adjacent the proximal ring 522 of the filter 520. In the device 510, the distal ring 524 is free to slide along the catheter shaft 512, such that when the balloon 536 is inflated and forces the ribs 526 to bow outward, the distal ring 524 slides in a proximal direction, as indicated by the arrow 539 as shown in FIG. 15, permitting the filter 520 to raise.

Figure 16:
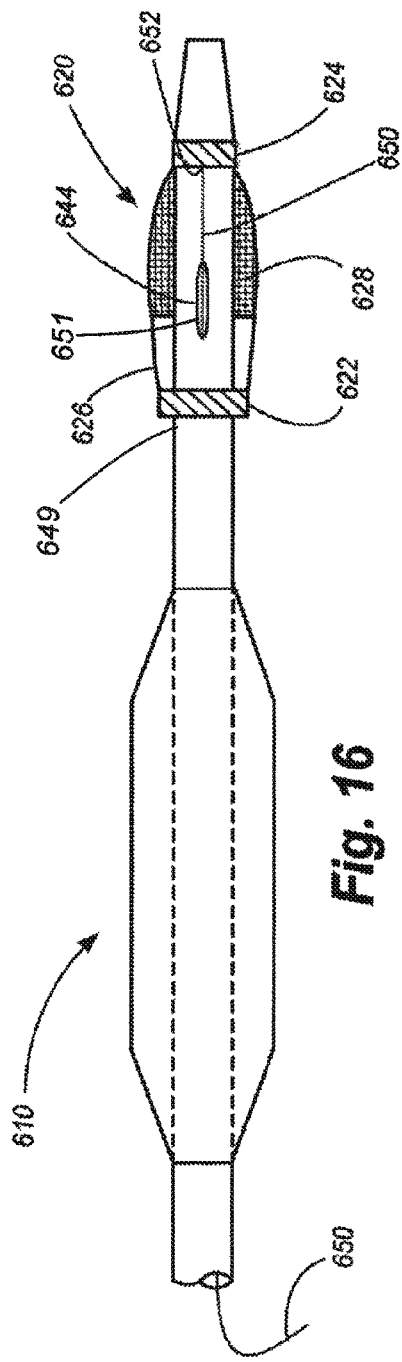
FIG. 16 is still another embodiment of a percutaneous transluminal angioplasty device according to the present invention. This embodiment employs a pull wire operable from outside the patient which is attached to a front ring of the embolic filter. When the physician exerts tension on the wire, the distal ring is displaced proximally, bringing it closer to the proximal ring, thereby causing the ribs to bow outward and thereby erecting the embolic mesh filter.
Figure 17:
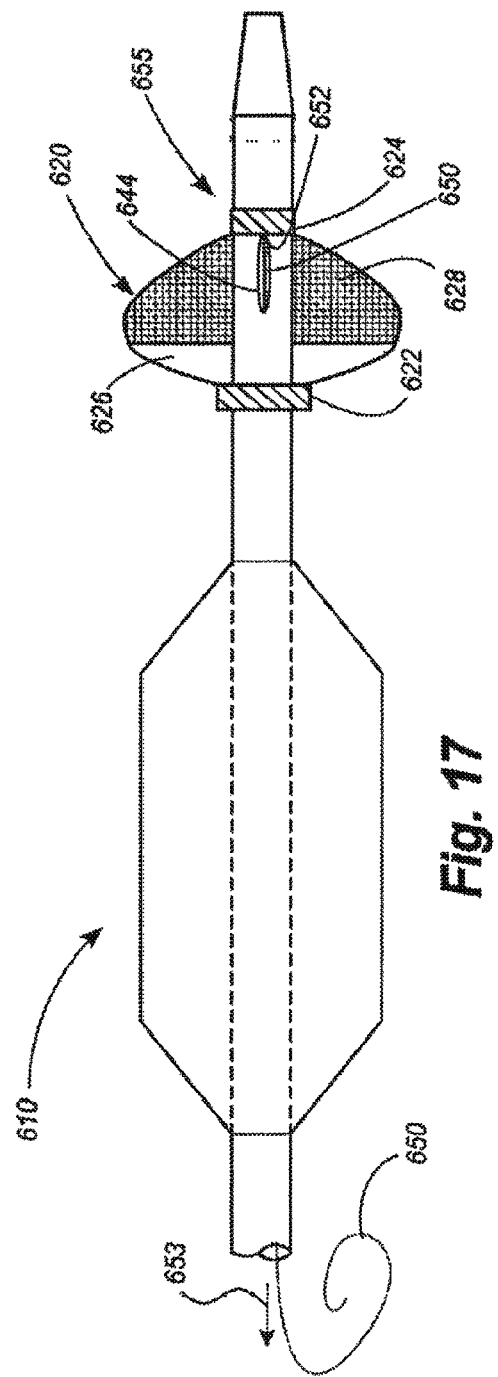
FIG. 17 is a different view of the embodiment of FIG. 16 and shows the angioplasty balloon inflated and the embolic filter erected.

The embodiment 610 shown in FIGS. 16 and 17 employs a different means for erecting the filter 620. In the embodiment 610 a pull wire 650 is used. The pull wire 650 extends through what would formerly have been used as the filter balloon inflation lumen 644, and the distal end 652 of the pull wire 650 is attached to the distal ring 624. When the physician wishes to raise the filter 620, he exerts a tension on the wire 650, as indicated by the arrow 653, thus drawing the distal ring 624 in a proximal direction as indicated by the arrow 655 toward the proximal ring 622. The ribs bow outward, erecting the filter mesh 628 as shown in FIG. 17.

In the device 710 shown in FIGS. 18 and 19, the distal end 752 of a push wire 750 is attached to the proximal ring 722. Thus when the wire 750 is pushed in the direction indicated by the arrow 753, the proximal ring 722 is advanced distally toward the distal ring 724 in the direction indicated by the arrow 755, causing the ribs 726 to bow outward and thereby erecting the filter 720, as shown in FIG. 19.

Figure 20:
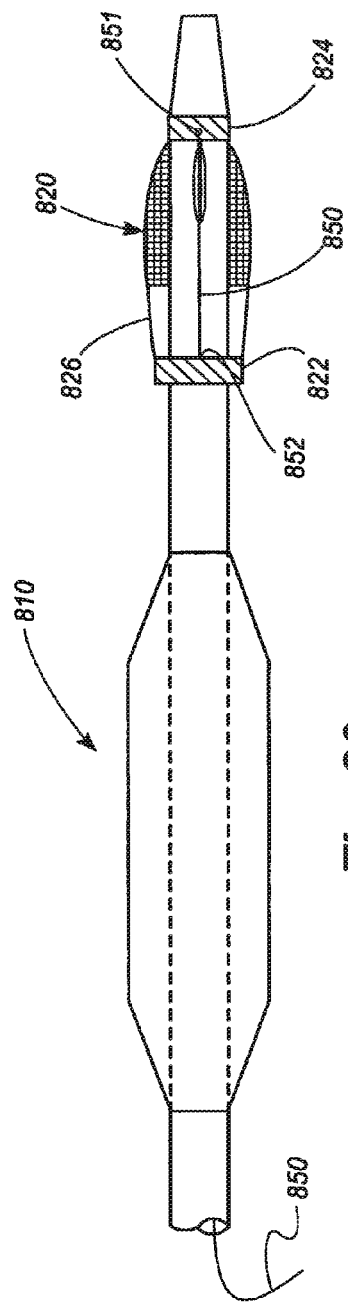
FIG. 20 is yet another embodiment of a percutaneous transluminal angioplasty device according to the present invention, showing the angioplasty balloon and the embolic filter in their collapsed conditions.
Figure 21:
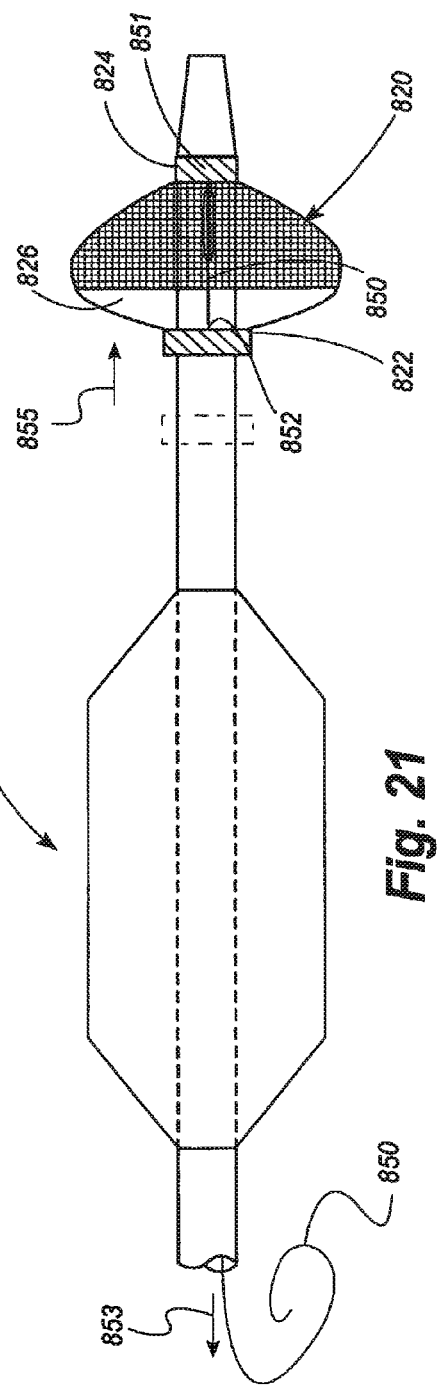
FIG. 21 is another view of the embodiment of FIG. 20, showing the angioplasty balloon inflated and the embolic filter raised.

The device 810 shown in FIGS. 20 and 21 uses a pull wire 850 to erect the filter 820. The pull wire 850 wraps around an opening 851 in the stationary distal ring 824 and extends rearward toward the proximal ring 822 to which the distal end 852 of the pull wire is attached. Thus when tension is exerted on the pull wire 850 in the direction indicated by the arrow 853, the proximal ring 822 is drawn distally toward the distal ring 824 in the direction indicated by the arrow 855, causing the ribs 826 to bow outward and thereby erecting the filter 820, as shown in FIG. 21.

Figure 22:
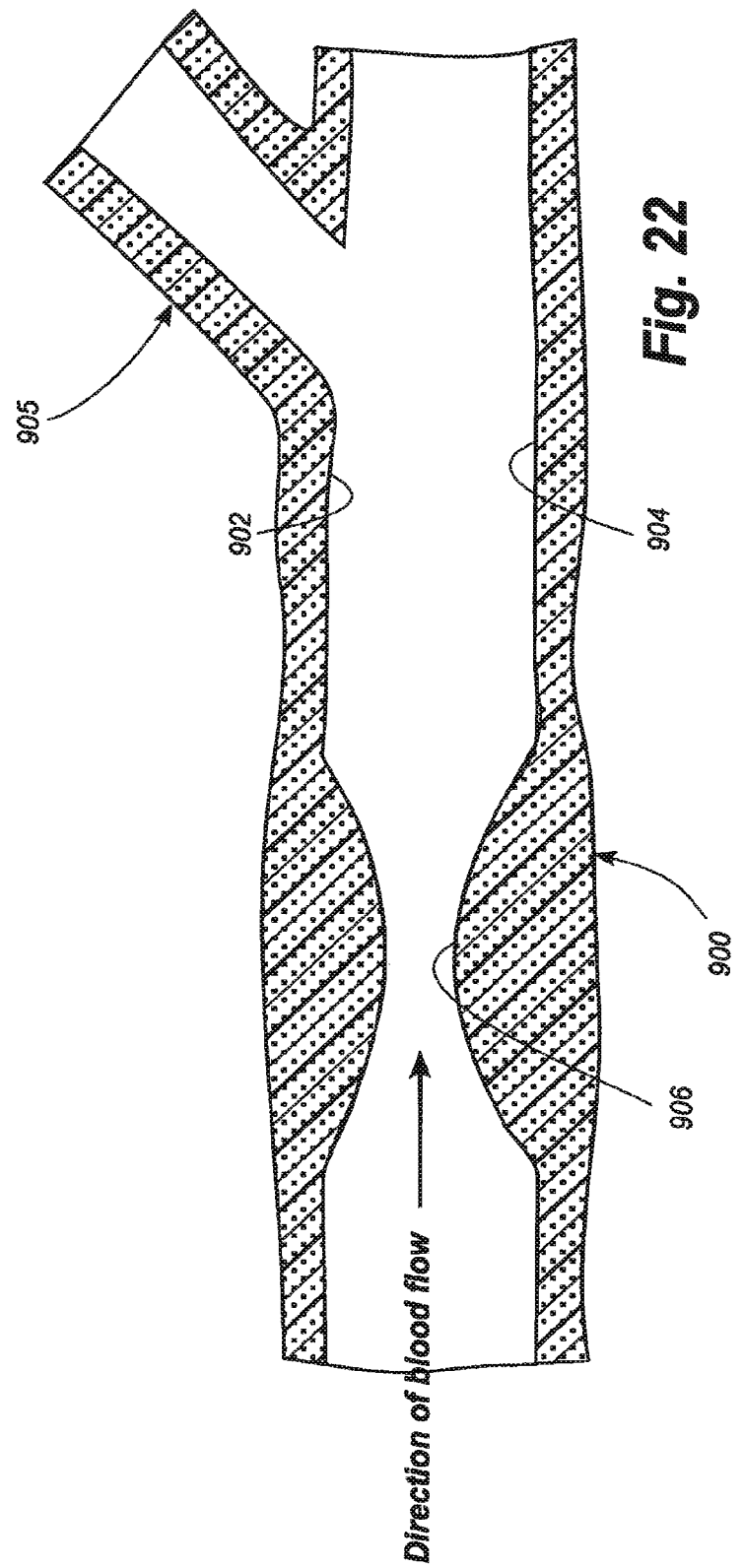
FIG. 22 shows a side cut away view of a coronary artery with a stenosis.

The operation of the device 10 will now be explained with respect to FIGS. 22-25, and it will be understood that the other devices operate on a substantially the same principles. FIG. 22 shows a vascular structure (e.g., coronary artery, saphenous vein graft, renal artery, carotid artery, superficial femoral artery, etc.) 900 with upper and lower walls 902, 904, a branch vessel 905, and a stenosis or blockage 906 caused by the build-up of plaque or other substances on the arterial walls in such a way as to narrow the diameter of the arterial lumen, and m the process, constrict the flow of blood therethrough.

Figure 23:
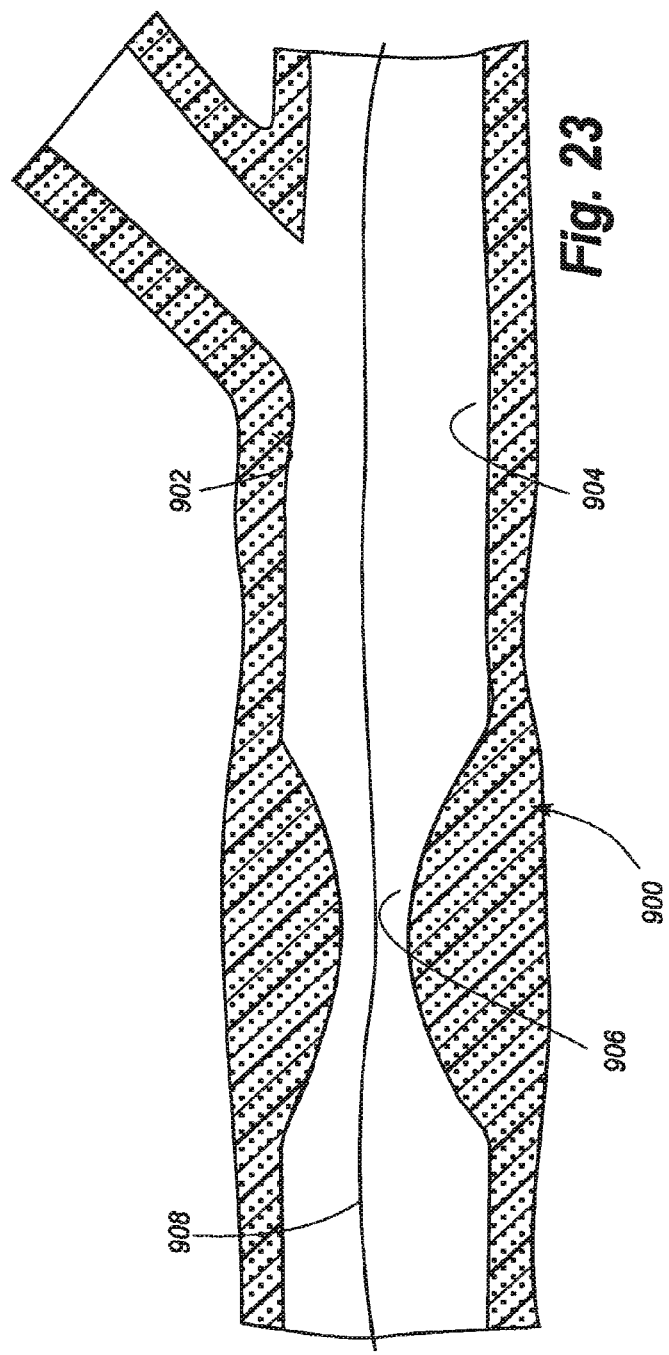
FIG. 23 shows the coronary artery of FIG. 20 with a guide wire fed through the coronary artery and through the stenosis.

In FIG. 23, a guide wire 908 has been inserted by the physician, such as through the femoral artery, and guided through the vascular system until the guide wire passes through the stenosis 906 in the vascular structure 900.

Figure 24:
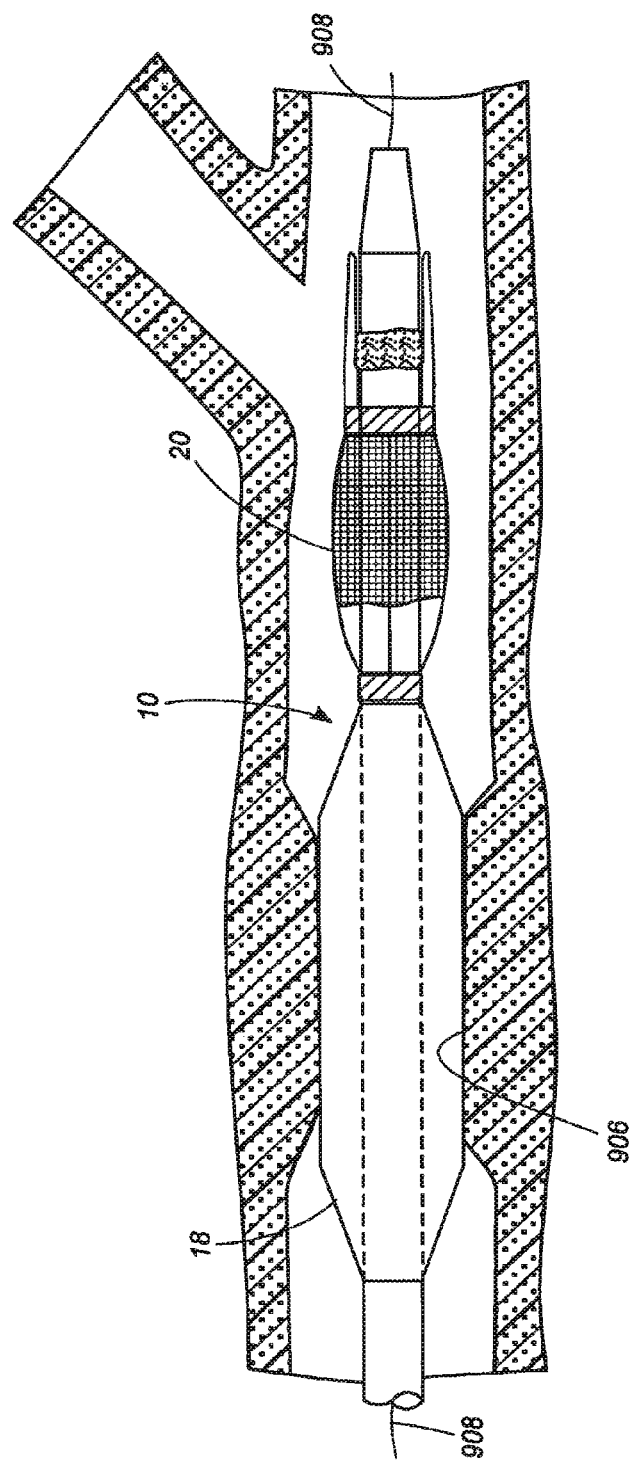
FIG. 24 shows the device of FIG. 1 threaded over the guide wire of FIG. 23 and positioned such that the angioplasty balloon is located within the stenosis.

Referring now to FIG. 24, the apparatus 10 has been inserted over the guide wire 908 and advanced to a location wherein the angioplasty balloon resides within the stenosis 906. The embolic filter 20 resides a few centimeters distal or downstream from the angioplasty location. In FIG. 24 both the angioplasty balloon and the embolic filter are shown in their collapsed conditions.

Figure 25:
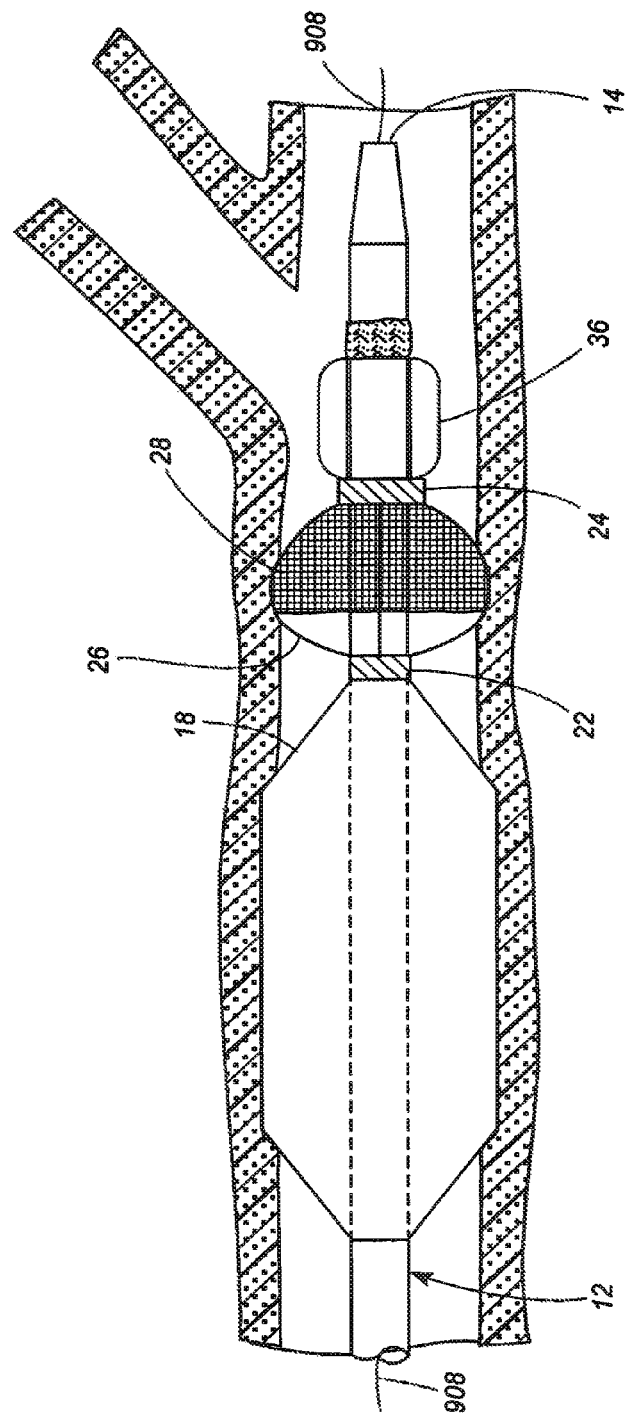
FIG. 25 illustrates the angioplasty balloon in its inflated condition to reduce the stenosis, and the embolic filter has been erected to capture any embolic particles that may break loose into the blood stream as a result of the angioplasty procedure.

In FIG. 25 the embolic filter 20 has been erected by inflating the filter balloon 36, causing the distal ring 22 to slide in a proximal direction along the catheter shaft 12. As the ribs 26 bow outward, the mesh filter material 28 supported by the ribs spreads so as to cover substantially the entire arterial lumen. The angioplasty balloon 18 is now inflated. As the balloon 18 inflates, it pushes tissue and plaque forming the stenosis 906 outward, opening the stenosis and possibly loosening embolic particles in the process. Any such embolic particles which get captured in the blood stream will be caught by the embolic filter 20 and will thereby be prevented from traveling to a location where they can cause clinical damage.

Of interest in FIG. 25 is the close proximity in which the filter 20 is erected relative to the stenosis 906. Despite the short "landing area" between the stenosis 906 and the branch vessel 905, the filter 20 is erected to capture embolic particles upstream of the branch vessel.

When removing the device 10 from the coronary artery, the preferred procedure is to deflate the angioplasty balloon 18 to first, prior to collapsing the embolic filter 20. In this way, any embolic particles that are broken loose as the angioplasty balloon 18 deflates will be captured by the filter 20. The embolic filter balloon 20 is then deflated; permitting the ribs 26 and filter mesh 28 to collapse against the shaft 14 of the catheter 12. Any embolic particles captured by the mesh 28 are trapped against the shaft 14. The device 10 is then withdrawn over the guide wire 908 and removed from the patient's body.

Figure 26:
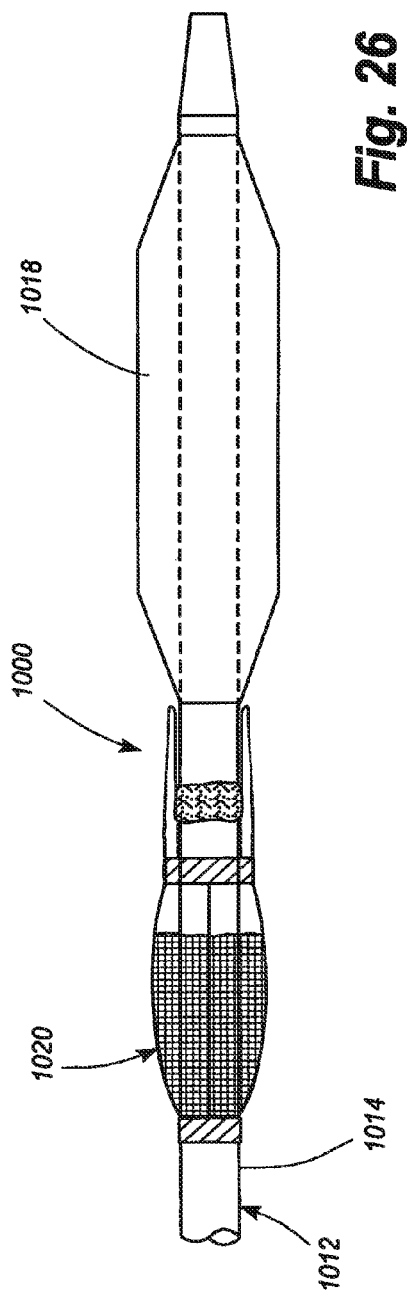
FIG. 26 is a partial cut away side view of an embodiment of a device in which the angioplasty balloon and embolism filter, shown in their collapsed positions, are reversed on the catheter shaft for peripheral vascular applications in which blood flows in the opposite direction.
Figure 27:
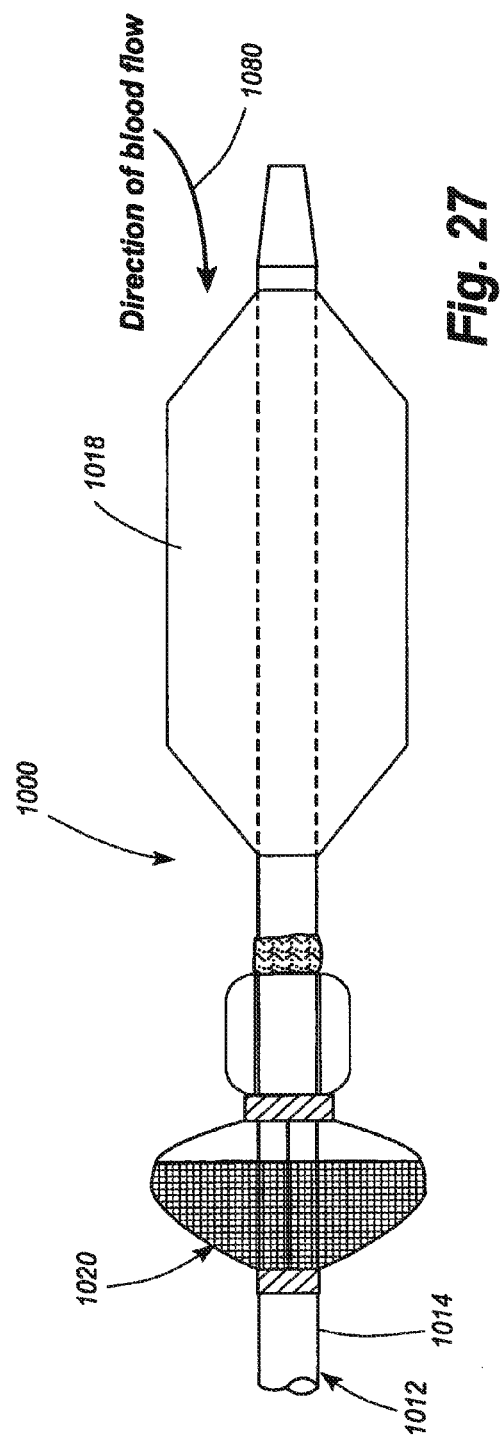
FIG. 27 is a partial cut away side view of the device of FIG. 26 showing the angioplasty balloon and embolism filter in their erected positions.

In various peripheral vascular applications, it may be necessary to insert the catheter against the direction of blood flow (e.g., the aorta). FIGS. 26 and 27 illustrate a device 1000 in which the angioplasty balloon 1018 and the embolic filter 1020 are reversed on the shaft 1014 of the catheter 1012. Thus with the blood flowing within the vessel in the direction indicated by the arrow 1080, the embolic filter 1020 will be proximal to the angioplasty balloon 1018 and thus positioned to capture any embolic particles that may be dislodged by the angioplasty balloon.

While the embodiment 1000 of FIGS. 26 and 27 employs the same method and device for erecting the embolic filter as the embodiment 10 of FIGS. 1-3, it will be understood that the methods and devices for erecting the embolic filter of other embodiments disclosed above are equally applicable to a configuration like the device of embodiment 1000 where the angioplasty balloon is positioned between the embolic filter and the tip of the device.

Figure 28:
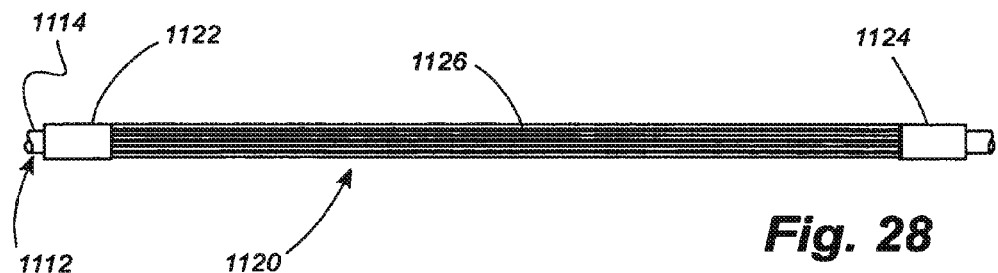
FIG. 28 is a side view of an embolism filter according to another embodiment of the present invention.
Figure 29:
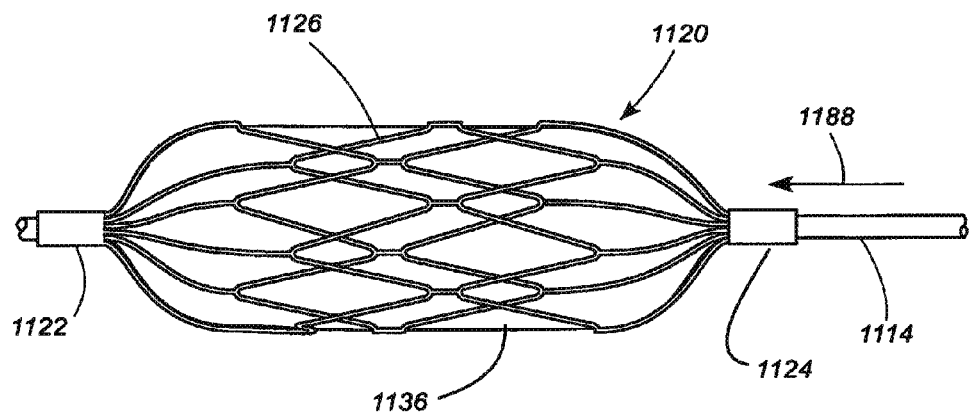
FIG. 29 is a side view of the embolism filter of FIG. 28 with the inflation balloon expanded to erect the embolism filter; filter mesh is shown removed to reveal interior detail.
Figure 30:
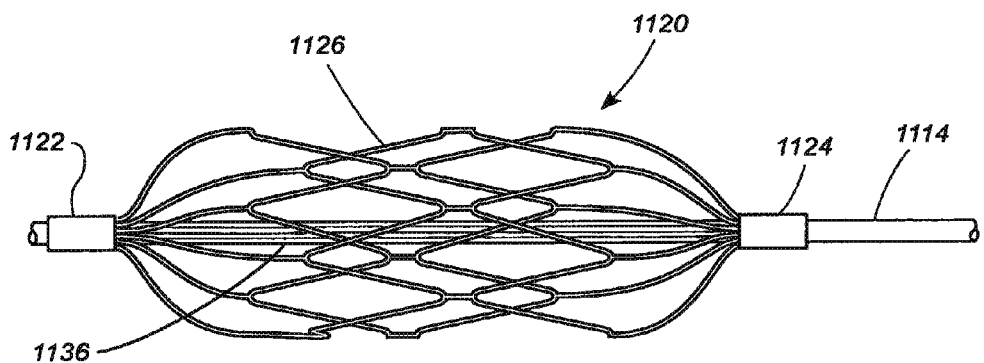
FIG. 30 is a side view of the embolism filter of FIG. 28 with the inflation balloon deflated; filter mesh is shown removed to reveal interior detail.
Figure 31:
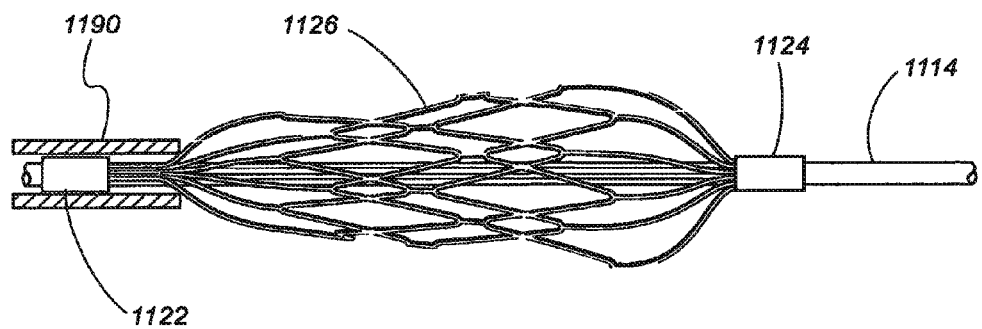
FIG. 31 is a side view of the embolism filter of FIG. 28 being retracted into the forward end of a catheter to collapse the filter; filter mesh is shown removed to reveal interior detail.

FIGS. 28-32 show still another embodiment of an embolic filter 1120 for use in conjunction with an angioplasty balloon. FIGS. 28-32 show only the embolic filter 1120 and not the angioplasty balloon, but it will be understood that the embolic filter is located on the same catheter 1114 as the angioplasty balloon in the same manner as the embodiments previously disclosed. Further, FIGS. 29-31 show the embolic filter 1120 without its filter mesh 1128 for clarity of illustration.

In FIG. 28 the embolic filter 1120 is folded closely against the shaft of the catheter 1112. The ribs 1126 of the filter 1120 extend between a proximal ring portion 1122 and a distal ring portion 1124. The distal ring portion 1124 is slidably mounted on the shaft 1114 of the catheter 1112, and the proximal ring portion 1122 is fixed with relation to the shaft of the catheter. In FIG. 29 the embolic filter balloon 1136 has been inflated, embolic filter. As the ribs expand, the distal ring portion 1124 slides in the proximal direction, as shown by the arrow 1188. Once expanded, the ribs 1126 maintain their shape, such that when the embolic filter balloon 1136 is deflated, as shown in FIG. 30, the embolic filter 1120 remains expanded.

To retract the embolic filter 1120, a second, outer catheter 1190 is advanced over the catheter 1112, as shown in FIG. 31, causing the ribs 1126 to collapse as the embolic filter is withdrawn into the forward end of the outer catheter 1190. As the ribs 1126 collapse, the distal ring portion 1124 slides in the distal direction. Once the embolic filter 1120 has been completely retracted into the forward end of the outer catheter 1190, the outer and inner catheters are withdrawn simultaneously.

Figure 32:
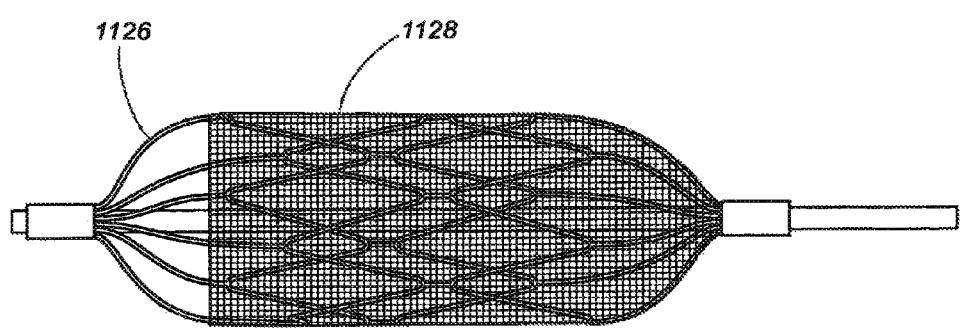
FIG. 32 is a side view of the embolism filter of FIG. 28, with the filter expanded and filter mesh in place.

FIG. 32 shows the embolic filter 1120 with filter mesh 1128 positioned over the ribs 1126.

FIGS. 33 and 34 illustrate a further embodiment of a percutaneous angioplasty device 1210, in which the embolic filter 1220 is located on a different carrier than the angioplasty balloon 1218. Specifically, the angioplasty balloon 1218 is located on an outer catheter 1294, and the embolic filter 1220 is located at the forward end of an inner catheter 1295 (the embolic filter 1220 is shown without filter mesh in FIGS. 33 and 34 for clarity of illustration.) The outer catheter preferably has three lumens, one for inflating the angioplasty balloon 1218, one for accommodating a guide wire (not shown), and one for receiving the inner catheter 1295 and embolic filter 1220. The inner catheter 1295 is slidably telescopically disposed within the outer catheter 1294. The ribs 1226 of the embolic filter 1220 are formed from a shape-memory metal such as nitinol and are constructed to normally assume an "open" configuration. When retracted within the forward end of the outer catheter 1294, the ribs 1226 of the embolic filter collapse.

To use the percutaneous angioplasty device 1210, the inner catheter is inserted into the outer catheter so that the embolic filter 1220 is collapsed within the distal end of the device, as shown in FIG. 33. The outer and inner catheters 1294, 1295 are inserted together, such as through the femoral artery, over a guidewire and advanced through the vascular system to a location wherein the un-inflated angioplasty balloon 1218 resides within the stenosis. Once location of the angioplasty balloon 1218 within the stenosis has been verified by suitable medical imaging technology, the inner catheter is advanced to progress the embolic filter 1220 beyond the forward end of the outer catheter 1294. As the embolic filter 1220 is freed from the confines of the outer catheter 1294, the ribs assume their expanded configuration and erect the embolic filter. Thereafter the angioplasty balloon 1218 may be inflated to treat the stenosis, and any emboli loosened during the procedure will be captured by the embolic filter 1220 downstream of the stenosis.

When the angioplasty procedure has been completed, the angioplasty balloon 1218 is deflated, and the embolic filter 1220 is withdrawn back into the forward end of the outer catheter 1294. The outer and inner catheters 1294, 1295 are then withdrawn together from the patient.

In the foregoing embodiment a wire can be substituted for the inner catheter 1295 as a means for carrying the embolic filter 1220.

Figure 35:
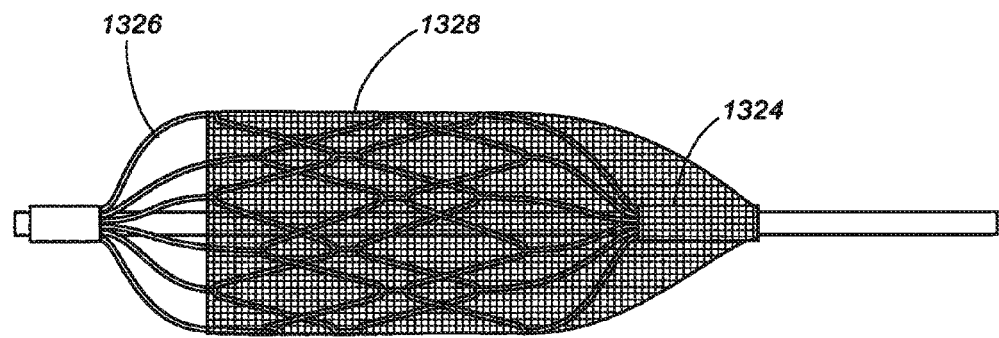
FIG. 35 is a side view of a further embodiment of an angioplasty device in which the filter mesh extends beyond the end of the ribs so as to form a sac when the filter is collapsed.
Figure 36:
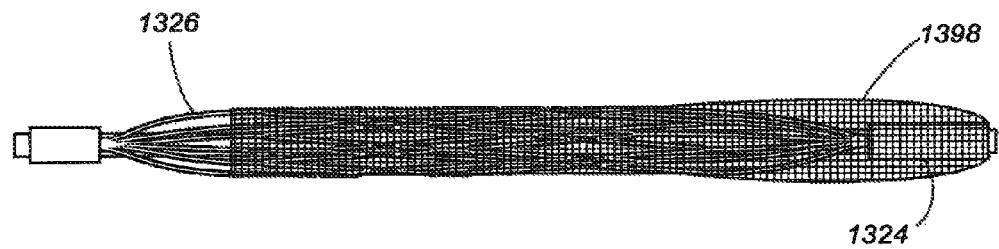
FIG. 36 shows the angioplasty device of FIG. 35 in a collapsed configuration.

FIGS. 35 and 36 show an angioplasty device 1310 that is identical to the device 10, with the exception that the filter mesh 1328 extends distally beyond the end of the ribs 1326 and is attached to the distal end of the distal ring 1324. When the filter 1320 is collapsed, as shown in FIG. 36, a sac 1398 is formed which helps contain the embolic particles, thereby minimizing the possibility that the ribs 1326 will squeeze the particles out of the filter.

In each of the foregoing examples, it will be appreciated that an angioplasty balloon is but one means for relieving a stenosis in a vessel. Stents, mechanical thrombectomy devices, or other suitable apparatus may be substituted for the angioplasty balloon and positioned on the catheter at a location proximal to the embolic filter. Thus any emboli loosened by the stent or mechanical thrombectomy device will be captured by the embolic filter in the same manner as described above with respect to the angioplasty balloon.

While the foregoing disclosed embodiments comprise filter ribs of a shape memory metal such as nitinol, it will be appreciated that similar results can be obtained by using any suitable resilient material. The ribs would be formed straight, forced open by the balloon, and return to their normal shape as a result of the resiliency of the structure. Or, in the case of the embodiment of FIGS. 33 and 34, the ribs would be initially formed in an open position, deformed inwardly to fit within the outer catheter, and return to their normal open position when released from the confines of the outer catheter.

Variations in the design of the filter are also contemplated. For example, while both ends of the ribs 26 of the filter 20 are mounted to rings 22, 24, it will be appreciated that the ends of the ribs at the fixed end of the filter can be secured directly to the catheter shaft.

It will be appreciated that the present invention permits the placement of the embolic filter very close to the means for treating the stenosis. This has the effect of minimizing the "landing area" of the filter and also permits the protection of side branches, as shown in FIGS. 22-25.

Finally, it will be understood that the foregoing embodiments have been disclosed by way of example, and that other modifications may occur to those killed in the art without departing from the scope and spirit of the appended claims. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A percutaneous transluminal angioplasty device, comprising:
   an elongated catheter having proximal and distal ends and an outer side wall;
   an interventional device attached to the catheter adjacent the distal end thereof;
   a filter attached to the elongated catheter between the interventional device and the distal end of the catheter, the filter being collapsible for insertion of the distal end of the catheter into a blood vessel, and the filter being expandable to an expanded position to capture emboli released into a bloodstream by operation of the interventional device, wherein the filter comprises:
   a movable ring portion movably attached to the catheter;
   a fixed ring portion immovably attached to the catheter such that the movable ring portion is movable relative to the fixed ring portion, wherein the movable ring portion is distal to the fixed ring portion;
   a plurality of elongated ribs extending longitudinally between and attached to the fixed and movable ring portions, and a filter mesh overlying a portion of the ribs, wherein the ribs are formed of a shape memory material that urges the ribs into a collapsed position;

wherein the catheter further comprises a lumen and a port in communication with the lumen, the port comprising an aperture in the outer side wall of the catheter located distal to the fixed ring portion and proximal to the movable ring portion, and the lumen extending from a location proximate the proximal end of the catheter to the port; and an actuator wire having proximal and distal ends, the actuator wire extending through the lumen of the catheter, and the distal end of the actuator wire exiting the lumen of the catheter through the port, the distal end of the actuator wire being attached to the movable ring portion;

wherein, when the filter is in the collapsed position, pulling on the proximal end of the wire exerts a force on the movable ring portion in the proximal direction that moves the movable ring portion toward the fixed ring portion and causes the ribs to bow outward to expand the filter to the expanded position;

wherein, when the filter is in the expanded position, releasing tension on the wire permits the shape memory of the ribs to return the ribs to their normal, collapsed position, collapsing the filter.

2. The percutaneous transluminal angioplasty device of claim 1, wherein the interventional device comprises an angioplasty balloon.

3. The percutaneous transluminal angioplasty device of claim 1, wherein the interventional device comprises a stent.

4. The percutaneous transluminal angioplasty device of claim 1, wherein the interventional device comprises a mechanical thrombectomy device.

5. The percutaneous transluminal angioplasty device of claim 1, wherein the shape memory material comprises nitinol.

6. The percutaneous transluminal angioplasty device of claim 1, wherein filter mesh overlies a distal portion of the ribs, and wherein, in the expanded position, the ribs bow outward, radially expanding the filter mesh.

7. The percutaneous transluminal angioplasty device of claim 1, wherein the filter mesh extends beyond the ribs in a longitudinal direction relative to the longitudinal axis of the catheter, such that a sac is formed to retain embolic particles when the filter is in the collapsed position.

8. The percutaneous transluminal angioplasty device of claim 1, wherein the filter mesh overlies a distal portion of the ribs, and wherein, in the expanded position, the ribs bow outward, radially expanding the filter mesh.

9. A percutaneous transluminal angioplasty device, comprising:

an elongated catheter having proximal and distal ends;

an interventional device attached to the catheter adjacent the distal end thereof;

a filter attached to the elongated catheter between the interventional device and the distal end of the catheter, the filter being collapsible for insertion and removal of the distal end of the catheter into a blood vessel, and the filter being expandable to an expanded position to capture emboli released into a bloodstream by operation of the interventional device, wherein the filter comprises:

a movable ring portion movably attached to the catheter;

a fixed ring portion immovably attached to the catheter such that the movable ring portion is movable relative to the fixed ring portion;

a plurality of elongated ribs extending longitudinally between and attached to the fixed and movable ring portions; and a filter mesh overlying a portion of the ribs, wherein the ribs are formed of a shape memory material that urges the ribs into a collapsed position;

wherein the catheter further comprises a lumen extending from a location proximate the proximal end of the catheter, to a location distal to the interventional device; and an actuator wire having proximal and distal ends, the actuator wire extending through the lumen of the catheter, the proximal end of the actuator wire extending to a location proximate the proximal end of the catheter and the distal end of the actuator wire exiting the lumen through an aperture in an outer surface of a side wall of the catheter at a location distal to the interventional device, the distal end of the actuator wire being attached to the movable ring portion;

wherein when the filter is in a collapsed condition, manipulating the proximal end of the wire exerts a force on the movable ring portion that moves the movable ring portion toward the fixed ring portion and causes the ribs to bow outward to the expanded position.

10. The percutaneous transluminal angioplasty device of claim 9, wherein the movable ring portion is the distal ring portion.

11. The percutaneous transluminal angioplasty device of claim 10, wherein the aperture is distal to the proximal ring portion.

12. The percutaneous transluminal angioplasty device of claim 11, wherein the distal end of the actuator wire is operatively connected to the distal ring portion.

13. The percutaneous transluminal angioplasty device of claim 12, wherein pulling on the proximal end of the actuator wire draws the distal ring portion toward the fixed proximal ring portion.

14. The percutaneous transluminal angioplasty device of claim 9, wherein the movable ring portion is the proximal ring portion.

15. The percutaneous transluminal angioplasty device of claim 14, wherein the aperture is proximal to the proximal ring portion.

16. The percutaneous transluminal angioplasty device of claim 15, wherein the distal end of the actuator wire is operatively connected to the proximal ring portion.

17. The percutaneous transluminal angioplasty device of claim 16, wherein pushing on the proximal end of the actuator wire moves the proximal ring portion toward the fixed distal ring portion.

18. The percutaneous transluminal angioplasty device of claim 14, wherein the distal end of the actuator wire exits the lumen through the catheter side wall at a location distal to the proximal ring portion.

19. The percutaneous transluminal angioplasty device of claim 18, wherein the distal end of the actuator wire passes through an opening defined by the fixed distal ring portion and then is operatively connected to the proximal ring portion.

20. The percutaneous transluminal angioplasty device of claim 9, wherein the interventional device comprises a stent.

21. The percutaneous transluminal angioplasty device of claim 9, wherein the interventional device comprises a mechanical thrombectomy device.

22. The percutaneous transluminal angioplasty device of claim 9, wherein the shape memory material comprises nitinol.

23. The percutaneous transluminal angioplasty device of claim 19, wherein pulling on the proximal end of the actuator wire moves the proximal ring portion toward the fixed distal ring portion.

24. The percutaneous transluminal angioplasty device of claim 9, wherein the interventional device comprises an angioplasty balloon.

\* \* \* \* \*